United States Patent [19]

Alper et al.

[11] Patent Number: 5,457,229
[45] Date of Patent: Oct. 10, 1995

[54] PROCESS FOR PREPARING ISOCYANATES FROM URETHANES BY A NOVEL TECHNIQUE

[75] Inventors: Howard Alper; Valli Velaga, both of Ottawa, Canada

[73] Assignee: University of Ottawa, Ottawa, Canada

[21] Appl. No.: 194,229

[22] Filed: Feb. 9, 1994

[51] Int. Cl.$^6$ ................................................. C07C 263/04
[52] U.S. Cl. ................................................................ 560/345
[58] Field of Search ............................................ 560/345

[56] References Cited

U.S. PATENT DOCUMENTS 5,212,306  5/1993  Savoca et al. .......................... 544/193

OTHER PUBLICATIONS

V. L.. K. Valli et al. "Reductive carbonylation of . . . " J. Am. Chem. Soc., vol. 115 No. 9, 1993, pp. 3778–3779.
Y. Kumagai et al. Japan Patent, JP 01,135,753; Chem. Abstr. 1990, 112, Abstract #36703b.
T. Takano et al, Japan Patent, JP 01, 113,358, Chem. Abstr. 1989, 111 Abstract #19558e.
T. Takano et al, Japan Patent, JP 63,150,255, Chem. Abstr. 1989, 110, Abstract #58270u.
R. J. Spohn, GB Pat. Appl., GB 2,113,673, Chem. Abstr. 1984, 100 Abstract #7361k.
R. J. Spohn, Ger. Pat., DE 3,204,973, Chem. Abstr. 1983, 99, Abstract #213033u.
S. Okuda, Japan Patent, JP 57, 158,747, Chem. Abstr. 1983, 99, Abstract #105872h.
S. Okuda, Japan Patent, JP 57, 158,748, Chem. Abstr. 1983, 98, Abstract #160402j.
S. Fukuoka et al, Japan Patent, JP 60,237,058, Chem. Abstr. 1986, 104, Abstract #207855u.
T. R. Henson et al, U.S. Pat. No. 4,294,774, Chem. Abstr., 96, Abstract #7220n.
F. Merger et al, Ger. Pat. 2,942,543, Chem. Abstr., 1981, 95, Abstract #63133c.
F. Merger et al, Ger. Pat. 2,942,503, Chem. Abstr, 1981, 95, Abstract #25868p.
J. Disteldorf et al, Ger. Pat. DE 3,151,855, Chem. Abstr., 1983, 99, Abstract #176959c.
R. K. Boeckman et al. "Catechol boron halides: . . . " Tetrahedron Letter, 1985, 26, pp. 1411–1414.
S. Okuda, Japan Patent JP 57,158,746, Chem. Abstr. 1983, 98, Abstract #144386b.

*Primary Examiner*—José G. Dees
*Assistant Examiner*—Samuel Barts
*Attorney, Agent, or Firm*—Nixon & Vanderhye

[57] ABSTRACT

Urethanes are converted to isocyanates by reaction with a chloro-, bromo- or iodo-borane compound and a tertiary amine in a nonpolar solvent. With the preferred borane compound, chlorocatecholborane, the reaction goes speedily and under gentle conditions to give the isocyanate in good yield. Also formed is a borate which can be readily converted to the borane compound, for reuse.

18 Claims, No Drawings

PROCESS FOR PREPARING ISOCYANATES FROM URETHANES BY A NOVEL TECHNIQUE

The present invention relates to the preparation of isocyanates.

BACKGROUND INVENTION

Polyurethanes are employed, for instance, in paints, in plastics, in elastomers, in foams, in adhesives and in many other materials. Polyurethanes are made by reacting isocyanates, mainly diisocyanates, with polyols, the isocyanate moieties reacting with hydroxy groups of the polyol to form urethane linkages. Isocyanates will also react with amines to form polyureas that find widespread applications in the same fields as polyurethanes. Isocyanates are therefore important compounds and the present invention provides a process for preparing isocyanates.

Urethanes can be regarded as esters of carbamic acids and one process for preparing isocyanates involves dealcoholysis of esters of carbamic acid, as shown in the following reaction:

(I)

Many attempts have been made to carry out this apparently simple process, but with only limited success. To achieve the required reaction it has been necessary to use stringent conditions, such as elevated temperature, usually above 300° C., or toxic materials as catalyst, for instance powdered boron, powdered bismuth, boron carbide, boron nitride, germanium oxide, or both elevated temperature and toxic catalyst. Expensive solvents have also been required but even so yields of isocyanate have been low. The processes have also suffered from the tendency of the formed isocyanate to decompose at higher temperatures to give low yields.

In a paper in Tetrahedron Letters, 1985, Vol. 26, No. 11, pp 1411–1414, Robert K. Boeckman Jr. and Joan C. Potenza describe use of catechol boron halides (chloride and bromide) for cleaving certain ester, ether and carbamate protecting groups under mild conditions. Footnote 5 to the paper indicates that the product of cleavage of a carbamate is an amine.

SUMMARY OF THE INVENTION

The present invention provides a process for preparing an isocyanate, which process comprises reacting a urethane with a chloro-, bromo- or iodo- borane and a tertiary amine in a nonpolar solvent.

In one embodiment the invention comprises reacting a compound containing one or more urethane moieties with a borane compound of the general formula (II)

(II)

in which X is chlorine, bromine or iodine and R is a divalent organic group that is saturated or forms part of an aromatic ring, the oxygen atoms being bonded to carbon atoms of group R that are vicinal or are separated by one carbon atom, the reaction being carried out in the presence of a tertiary amine and in a nonpolar solvent.

DESCRIPTION OF THE PREFERRED EMBODIMENTS

A preferred borane compound is chlorocatecholborane, a preferred tertiary amine is triethylamine and a preferred nonpolar solvent is toluene. For purposes of illustration a reaction using these materials, with a urethane of formula R'—NHC(O)OMe, is described as follows:

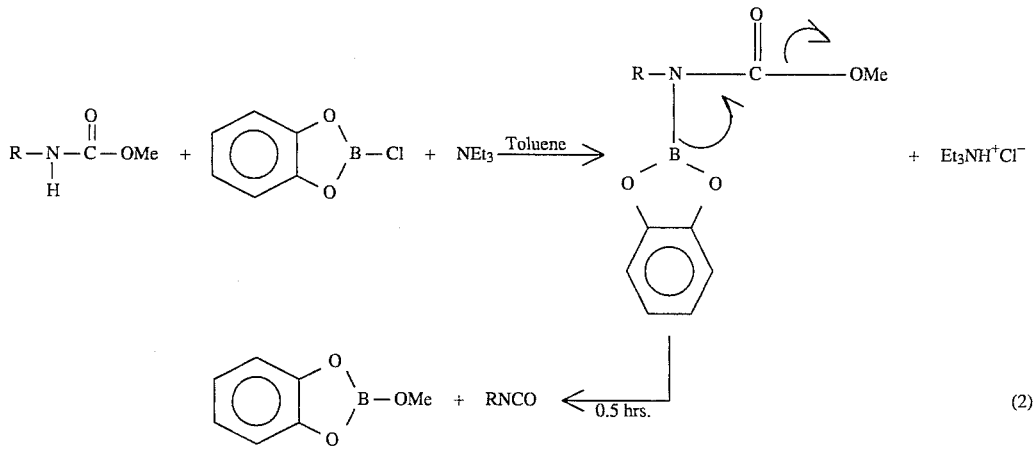

(2)

The reaction between the urethane and the chlorocatecholborane leads to the formation of the required isocyanate and formation of the trimethylammonium chloride salt. This salt precipitates from the nonpolar solvent toluene and can be separated easily. The reaction proceeds fairly rapidly to completion and isocyanate is formed in good yield. The precipitated salt appears as a white cloudy material, and cessation of formation of the precipitate indicates completion of the reaction. The reaction is simple and highly selective, When p-tolylmethylurethane was subjected to the reaction, refluxing for ten minutes afforded p-tolylisocyanate in 99% yield, p-Tolylethylurethane afforded p-tolylisocyanate in 100% yield. No side products, such as amines, were detected in either reaction.

The above equation suggests that the urethane, the borane compound and the tertiary amine should react in equimolar amounts. It is preferred that the borane compound and the tertiary amine should be present in amounts ranging from the stoichiometrically equivalent amounts up to about 1.5 times the stoichiometrically equivalent amounts. It is particularly preferred to use about 1.2 equivalents of borane compound and amine. If the urethane contains several urethane moieties, then the amounts of borane compound and amine are increased proportionally, e.g., for diurethanes and triurethanes they are doubled and tripled, respectively.

The reaction can be applied to any mono- or polyfunctional urethane, including diurethanes and triurethanes, that do not contain groups that will interfere with the course of the reaction. It has been applied successfully to obtain toluene 2,4- and 2,6-diisocyanates, p-phenylene-diisocyanate, the diisocyanate of Dytek-A (1,5-diamino-2-methylpentane), isophoronediisocyanate, Jeffamine D-400 and D-2000 diisocyanates and Jeffamine T-5000 triisocyanate. It is known that the compounds available under these Jeffamine trade marks are polymers with primary amine terminal groups and polypropyleneoxy backbones. Persons skilled in the art should have no difficulty in determining what groups present in the urethane may interfere with the course of the reaction. Often it will be possible to predict whether a group will interfere or not. In those cases where prediction is uncertain it will be a routine matter, not requiring exercise of any inventive faculty, to test by carrying out the process of the invention in accordance with the teaching of this specification and observe whether success is achieved.

The process of the invention can be described as the dealcoholysis of a urethane of formula R'NHCO$_2$R" by removal of the alcohol R"OH. The group R" can be, for example, an alkyl group, an aryl group such as phenyl or naphthyl, an aralkyl group such as benzyl or phenethyl or a cyclic or alicyclic group such as cyclohexyl or cyclopentyl. The reaction proceeds well when the alcohol being removed is a lower alkanol, for instance ethanol or methanol, and from this it can readily be predicted that the reaction will proceed well with higher alcohols.

As indicated, the preferred borane compound is chlorocatecholborane, i.e., a compound of the general formula (II) in which R is a phenyl group and X is chlorine. Chlorocatecholborane is available commercially, or it can be prepared from catechol and boron trichloride, as described by Boeckman and Potenza in Tetrahedron Letters, 1985, Vol. 26, No. 11, pp 1411–1414.

In general, it is preferred that in the borane compound X is chlorine, as chlorine is cheaper than bromine and iodine, and neither bromine nor iodine offers any compensating advantage over chlorine. Indeed, compounds in which X is iodine are more difficult to prepare, are very reactive and may present stability problems. It is preferred that the two oxygen atoms are bonded to two adjacent carbon atoms of the divalent organic group R so that there is formed a five-membered ring, as in catecholborane. It is possible, however, to use a borane compound in which the carbon atoms attached to the oxygen atoms are separated by one carbon atom, so that there is formed a six-membered ring. The precise structure of the divalent group R is not critical, provided that the borane compound does not contain groups that will interfere with the reaction. For this reason groups with active hydrogen atoms, e.g., hydroxy, amino, mercapto and carboxyl groups, must be avoided. R can be, for instance, a dimethylene, trimethylene, phenylene, naphthylene, cyclohexylene or decahydronaphthylene group. Hydrogen atoms in these groups can be replaced by various substituents that are free of active hydrogen, for instance, saturated aliphatic groups such as alkyl groups, aromatic groups such as phenyl and naphthyl, alicyclic groups such as cyclohexyl and cyclopentyl and aralkyl groups such as benzyl and phenethyl. Halogen substituents should be avoided, as these may compete with the halogen atom X for the organic base and thereby interfere with the course of the reaction.

Borane compounds containing aliphatic R groups can be prepared by reacting the corresponding diol R(OH)$_2$ with the boron halide BX$_3$. In some instances the borane compound will be very reactive, so that it has to be stored in solution. In such cases, the borane compound can be prepared in situ or can be used in solution, e.g., 1M solution. This is necessary, for instance, when ethylene glycol is used to form a chloroborane in which R is the dimethylene group. If the haloborane is to be stored suitable solvents include chlorohydrocarbons such as dichloromethane and dichloroethane. If the haloborane compound is prepared for use in situ then the solvent should be the solvent used for the dealcoholysis reaction, e.g., toluene.

The solvent is a nonpolar solvent. Some urethanes will dissolve in the solvent at room temperature but others, especially di- and triurethanes, may not be soluble at room temperature. In such cases gentle reflux of the solvent is necessary. Suitable nonpolar solvents include aromatic solvents such as toluene, benzene, xylenes and also saturated aliphatic solvents such as pentanes, hexanes and the like. In general, it is preferred that the nonpolar solvent is aromatic, as urethanes display better solubility in aromatic solvents. The most preferred solvent is toluene. It will of course be appreciated that the solvent must be dry, so that there is no reaction between the formed isocyanate and water in the reaction mixture. It is preferred to carry out the reaction under an inert gas, suitably argon or nitrogen.

The reaction is carried out in the presence of a tertiary amine. It is believed that any tertiary amine can be used but mention is made of triethylamine, diisopropyl ethylamine, pyridine, quinoline, bipyridine, DABCO (1,4-diazabicyclo[2.2.2]octene), DBN (diazabicyclononene) and DBU (1,8-diazabicyclo[5.4.0]undec-7-ene) as examples of suitable tertiary amines.

The reaction proceeds readily at room temperature and is suitably carried out at a temperature between ambient temperature and the reflux temperature of the reaction mixture. If desired, the isocyanate can be removed from the reaction mixture by distillation. If this is to be done there should be selected a nonpolar solvent whose boiling point is significantly above the boiling point of the isocyanate, so that the isocyanate distillate is not contaminated with solvent. The distillation can be carried out under reduced pressure if desired.

Alternatively, isocyanates can be recovered from the reaction mixture by being derivatized with a selected derivatizing agent, for instance a primary or secondary amine to form a urea, or an alcohol to form a urethane different, of course, from the original urethane. If the isocyanate product is a di- or triisocyanate then the derivatizing agent should be monofunctional, to avoid polymer format ion. The derivatizing agent must of course be dry, so that no moisture is added to react with the isocyanate.

The products of the reaction are the required isocyanate, the precipitated ammonium halide salt and a borate compound in which the halogen atom that was initially present has been replaced by a group derived from the alcohol portion of the original urethane. Such a borate compound can be readily converted again to the corresponding borane compound of formula (I) by hydrolysis to the corresponding diol (see E. J. Corey et. al., Tetrahedron Letters, Vol. 25, No. 1, pp 3–6), followed by reaction with $BX_3$.

The invention is further illustrated in the following examples:

Examples 1 to 15

The following general procedure was used: The urethane(1 mmol) was dissolved in dry toluene(2 mL), triethylamine(1.2 mmol) was added and the mixture was refluxed for 5 minutes($N_2$ atmosphere). Chlorocatecholborane(1.2 mmol) was added and the mixture was refluxed for another 5 minutes. After the addition of chlorocatecholborane, an instantaneous reaction was observed and a white cloudy solid suspension appeared in the reaction flask (due to the formation of $Et_3NH^+Cl^-$). Each reaction was monitored by infrared spectroscopy which showed disappearance of the peak due to urethane and appearance of a peak due to isocyanate. Each reaction was also monitored by gas chromatography and GC—Mass spectroscopy. The product isocyanate was isolated by vacuum distillation under $N_2$ atmosphere or derivatized as a urea using an amine, or as another alkylurethane by reacting with a different alcohol. In case of di- and triurethanes, correspondingly double and triple the amounts of chlorocatecholborane and triethylamine were used.

The results are given in Table 1, below

TABLE I

| Example | Substrate | Product[a] | $\nu_{CO}$ cm$^{-1}$ | Yield[b] (%) |
|---|---|---|---|---|
| 1. | H$_3$C—C$_6$H$_4$—NHCO$_2$Me | H$_3$C—C$_6$H$_4$—NCO | 2273 | 99 |
| 2. | H$_3$C—C$_6$H$_4$—NHCO$_2$Et | H$_3$C—C$_6$H$_4$—NCO | 2273 | 100 |
| 3. | 1-naphthyl-NHCO$_2$Me | 1-naphthyl-NCO | 2274 | 100[c] |
| 4. | 2-methyl-5-NHCO$_2$Me, 2-NHCO$_2$Me benzene | 2-methyl-5-NCO, 2-NCO benzene | 2268 | 100 |
| 5. | 2-methyl-1,3-bis(NHCO$_2$Me)benzene (MeO$_2$CHN, NHCO$_2$Me with CH$_3$) | 2-methyl-1,3-bis(NCO)benzene (OCN, NCO with CH$_3$) | 2268 | 100 |
| 6. | 1,3-bis(NHCO$_2$Me)benzene | 1,3-bis(NCO)benzene | 2264 | 98 |
| 7. | MeO$_2$CHN—C$_6$H$_4$—NHCO$_2$Me | OCN—C$_6$H$_4$—NCO | 2264 | 100 |
| 8. | MeO$_2$CHN—C$_6$H$_4$—C$_6$H$_4$—NHCO$_2$Me | OCN—C$_6$H$_4$—C$_6$H$_4$—NCO | 2266 | 99 |
| 9. | cyclohexyl-NHCO$_2$Me | cyclohexyl-NCO | 2261 | 98 |
| 10. | CH$_3$(CH$_2$)$_7$NHCO$_2$Me | CH$_3$(CH$_2$)$_7$NCO | 2272 | 96 |

TABLE I-continued

| Example | Substrate | Product[a] | $\nu_{CO}$ cm$^{-1}$ | Yield[b] (%) |
|---|---|---|---|---|
| 11. | MeO$_2$CHNCH$_2$CH(CH$_2$)$_3$NHCO$_2$Me[d]<br>       \|<br>      CH$_3$ | OCNCH$_2$CH(CH$_2$)$_3$NCO<br>    \|<br>   CH$_3$ | 2274 | 100 |
| 12. | MeO$_2$CHN–⟨cyclohexyl⟩–NHCO$_2$Me | OCN–⟨cyclohexyl⟩–NCO | 2271 | 100 |
| 13. | CH$_3$      CH$_3$<br>  \|          \|<br>H$_2$CO[CH$_2$CHO]$_x$CH$_2$CHNHCO$_2$Me<br>HCO[CH$_2$CHO]$_y$CH$_2$CHNHCO$_2$Me<br>    \|        \|<br>   CH$_3$   CH$_3$<br><br>H$_2$CO[CH$_2$CHO]$_z$CH$_2$CHNHCO$_2$Me<br>    \|        \|<br>   CH$_3$   CH$_3$ | CH$_3$      CH$_3$<br>  \|          \|<br>H$_2$CO[CH$_2$CHO]$_x$CH$_2$CHNHCO[e]<br>HCO[CH$_2$CHO]$_y$CH$_2$CHNHCO<br>    \|        \|<br>   CH$_3$   CH$_3$<br><br>H$_2$CO[CH$_2$CHO]$_z$CH$_2$CHNHCO<br>    \|        \|<br>   CH$_3$   CH$_3$ | 2255 | 96 |
| 14. | CH$_3$      CH$_3$<br>  \|          \|<br>MeO$_2$CHNCHCH$_2$[OCH$_2$CH]$_x$NHCO$_2$Me | CH$_3$      CH$_3$<br>  \|          \|<br>OCNCHCH$_2$[OCH$_2$CH]$_x$NCO[f] | 2258 | 97 |
| 15. | CH$_3$      CH$_3$<br>  \|          \|<br>MeO$_2$CHNCHCH$_2$[OCH$_2$CH]$_y$NHCO$_2$Me | CH$_3$      CH$_3$<br>  \|          \|<br>OCNCHCH$_2$[OCH$_2$CH]$_y$NCO[g] | 2259 | 96 |

[a]Products were characterized by comparison of spectral data (IR, MS, NMR) and retention times (gc) with authentic materials in most cases. Isocyanates in entries 1–6 and 9, 10 and 12 were commercially available. Isocyanates 7, 8$^{1b}$ and 11$_4$ are known compounds.
[b]Yields were determined by gas chromatography; [c]Isolated yield, 91%; [d]Dytek-A;
[e]Jeffamine triisocyanate, x + y + z = 5000.
[f]Jeffamine D-400 diisocyanate, x = 5.6
[g]Jeffamine D-2000 diisocyanate, y = 33 avg.

Example 16

Example 3 was carried out as described above but using benzene, instead of toluene, as nonpolar solvent. The results obtained were the same as those given above for Example 3.

Example 17

The supernatant solution from Example 3 was taken out under nitrogen, poured into an excess of dry ethanol and the solvent was removed. A white solid material was obtained, composed of triethylammonium chloride salt and 1-naphthyl ethyl urethane. The solid material was washed with a mixture of 2% ethanol in hexane, which dissolved the urethane, leaving the salt. The structure of the 1-naphthyl ethyl urethane was confirmed by IR and NMR and the yield was 92%.

Example 18

Ethylene glycol was reacted with boron trichloride to form the borane compound of formula

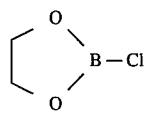

(For detailed procedure see Genmarie et. al., Tetrahedron Letters, 1984, 25, 2279). To a solution of p-tolyl methyl urethane there were added the borane compound and triethylamine and the mixture was refluxed for 5 minutes (N$_2$ atmosphere). An instantaneous reaction was observed and a white cloudy suspension appeared in the reaction flask, due to the formation of Et$_3$NH$^+$Cl$^-$. p-Tolyl isocyanate was obtained and IR spectra showed the complete disappearance of urethane moieties and the formation of isocyanate moieties.

What is claimed is:

1. A process for preparing an isocyanate, which process comprises reacting a urethane with a chloro-, bromo- or iodo-borane and a tertiary amine in a nonpolar solvent.

2. A process according to claim 1 wherein the borane is a compound of the general formula (II)

(II)

in which X is chlorine, bromine or iodine and R is a divalent organic group that is saturated or forms part of an aromatic ring, the oxygen atoms being bonded to carbon atoms of group R that are vicinal or are separated by one carbon atom.

3. A process according to claim 1 wherein the borane is chlorocatecholborane.

4. A process according to claim 1 wherein the tertiary amine is triethylamine.

5. A process according to claim 1 wherein the nonpolar solvent is an aromatic solvent.

6. A process according to claim 1 wherein the nonpolar solvent is toluene.

7. A process according to claim 1 wherein the urethane is a methyl or ethyl ester of a carbamic acid.

8. A process according to claim 1 wherein the reaction is carried out under reflux conditions.

9. A process according to claim 1 which includes the further step of hydrolysing the borate formed, converting it to borane compound of general formula (II) and recycling it to the reaction.

10. A process according to claim 1 wherein p-tolylmethyl urethane ester is converted to p-tolylisocyanate.

11. A process according to claim 1 wherein toluene-2,4-diurethane is converted to toluene-2,4-diisocyanate.

12. A process according to claim 1 wherein toluene-2,6-diurethane is converted to to toluene-2,6-diisocyanate.

13. A process according to claim 1 wherein 1,4-phenylene-diurethane is converted to 1,4-phenylene diisocyanate.

14. A process according to claim 1 wherein 2-methylpentane-1,5-diurethane is converted to 2-methylpentane-1,5-diisocyanate.

15. A process according to claim 1 wherein isophorone diurethane is converted to isophorone diisocyanate.

16. A process according to claim 1 wherein

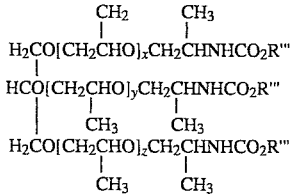

in which R''' is a methyl or ethyl group, x, y and z are integers and the sum x+y+z equals approximately 5,000, is converted into

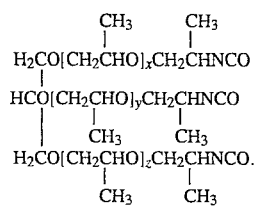

17. A process according to claim 1 wherein

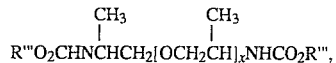

in which R''' is a methyl or ethyl group, x is an integer having a value of approximately 5–6, is converted into

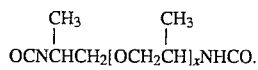

18. A process according to claim 1 wherein

in which R''' is a methyl or ethyl group, y has an average value of about 33, is converted into

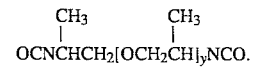

* * * * *

UNITED STATES PATENT AND TRADEMARK OFFICE
CERTIFICATE OF CORRECTION

PATENT NO. : 5,457,229
DATED : October 10, 1995
INVENTOR(S) : Alper et al

It is certified that error appears in the above-identified patent and that said letters patent is hereby corrected as shown below:

Column 5 line 2, delete "(I)" and replace by --(II)--.

Signed and Sealed this

Second Day of April, 1996

Attest:

BRUCE LEHMAN

*Attesting Officer*     *Commissioner of Patents and Trademarks*